(12) United States Patent
Hendriksen et al.

(10) Patent No.: US 9,089,672 B2
(45) Date of Patent: Jul. 28, 2015

(54) INTRODUCER PLACEMENT SYSTEM

(75) Inventors: Per Hendriksen, Herlufmagle (DK); Kasper Klausen, Helsinge (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 331 days.

(21) Appl. No.: 13/614,493

(22) Filed: Sep. 13, 2012

(65) Prior Publication Data

US 2013/0079809 A1  Mar. 28, 2013

(30) Foreign Application Priority Data

Sep. 23, 2011 (GB) .................................. 1116454.8

(51) Int. Cl.
*A61M 25/02* (2006.01)
*A61M 25/06* (2006.01)

(52) U.S. Cl.
CPC ......... *A61M 25/02* (2013.01); *A61M 2025/024* (2013.01); *A61M 2025/0681* (2013.01)

(58) Field of Classification Search
CPC ........... A61B 17/3439; A61B 17/3421; A61B 17/3415; A61M 25/02; A61M 2025/0681; A61M 2025/024
USPC .......... 606/108, 194, 200; 604/174, 175, 177, 604/178, 179; 600/585; 285/244
See application file for complete search history.

(56) References Cited

U.S. PATENT DOCUMENTS

| | | | |
|---|---|---|---|
| 972,372 A * | 10/1910 | Harding | 285/244 |
| 3,896,527 A | 7/1975 | Miller et al. | |
| 4,099,298 A | 7/1978 | Gimenez | |
| 4,425,682 A * | 1/1984 | Hashimoto et al. | 24/20 S |
| 5,074,870 A | 12/1991 | Von Zeppelin | |
| 5,505,714 A | 4/1996 | Dassa et al. | |
| 5,873,813 A | 2/1999 | Weiss | |
| 5,979,020 A | 11/1999 | Kimura et al. | |
| 6,497,010 B1 | 12/2002 | Klor et al. | |
| 2004/0043052 A1 * | 3/2004 | Hunter et al. | 424/426 |
| 2009/0259285 A1 * | 10/2009 | Duane et al. | 623/1.11 |

FOREIGN PATENT DOCUMENTS

| | | |
|---|---|---|
| FR | 835695 A | 3/1938 |
| FR | 2288904 A1 | 7/1974 |
| FR | 2571792 A1 | 10/1984 |
| FR | 2637350 A1 | 9/1988 |
| FR | 2756878 A3 | 12/1996 |
| GB | 190813370 | 6/1908 |
| WO | WO 2009/055739 A1 | 4/2009 |

OTHER PUBLICATIONS

Combined Search and Examination Report mailed Dec. 22, 2011, for related UK Patent Application No. GB1116454.8.

* cited by examiner

*Primary Examiner* — Thomas McEvoy
(74) *Attorney, Agent, or Firm* — Brinks Gilson & Lione

(57) ABSTRACT

An introducer assembly is provided with a sheath and a positioning device. The positioning device is able to be configured between released and locking conditions, wherein in the released condition the device can be slid along the outer sheath of the introducer. In the locked condition, the position device is locked to the sheath. The position device is used to fix the length of sheath which can be inserted into a patient and thereby to set the position of the distal end the sheath and thereby the position at which a medical device would be deployed in the patient. The positioning device includes a coil spring with a plurality of coil turns able to apply an even compressive force to the sheath in all radial directions in order to minimize the chance of collapse of the sheath as a result of compressive force.

20 Claims, 5 Drawing Sheets

INTRODUCER PLACEMENT SYSTEM

This application claims priority to GB application No. 1116454.8, filed Sep. 23, 2011, titled "Introducer Placement System", the contents of which are incorporated herein by reference.

TECHNICAL FIELD

The present invention relates to an introducer placement system for positioning an introducer assembly at the correct position with regard to a patient's anatomy. The preferred embodiments are designed for placement of a filter sheath used in the deployment of a vena cava filter, although could be used for any other type of deployment or introducer system.

BACKGROUND ART

The use of introducers for the performance of endoluminal medical treatments has become widespread as a result of the clinical and medical advantages over open surgical procedures. The use of introducers does, however, present difficulties, particularly with regard to accurate and reliable placement of the distal end of the introducer within the vasculature or other organs of the patient. While use of imaging methods such as fluoroscopy and X-ray or CRT imaging can enable the clinician to view the embedded distal end of the introducer in the patient, these imaging methods are not optimal. Ultrasonic imaging is a much more preferable imaging technique. However, introducer assemblies, particularly sheaths, catheters and the like, tend not to be readily visible by this technique. While it is possible to build into the introducer elements which are, for instance, radiopaque, this can typically affect the structure and performance of the device and is thus not always practical.

Various designs of introducer assemblies are disclosed, for example, in U.S. Pat. No. 4,425,682, U.S. Pat. No. 5,074,870, U.S. Pat. No. 5,873,813, U.S. Pat. No. 5,979,020, U.S. Pat. No. 6,497,010.

SUMMARY OF THE INVENTION

The present invention seeks to provide an improved introducer assembly, an improved vena cava deployment system and an improved method of placing a delivery sheath in a patient.

According to an aspect of the present invention, there is provided an introducer assembly including a sheath or catheter designed for endoluminal placement in a patient, and a positioning device locatable around the sheath or catheter, the positioning device including a locking device configurable between a locking condition and a releasing condition and including a coil spring provided with at least one turn, wherein the sheath or catheter is locatable within the at least one turn of the coil, the positioning device being movable along the sheath or catheter when the locking device is in the releasing condition and being fixed in position on the sheath or catheter when the locking device is in the locking condition, the at least one turn applying a substantially even radial compressive force to the sheath or catheter in all radial directions such that when in the locking condition the positioning device does not reduce the diameter of the sheath or catheter lumen, the positioning device being operable to mark and fix a percutaneous entry point of the sheath or catheter so as to fix the position of the latter in the patient.

This structure seeks to resolve the problem of accurate placement of a sheath of an introducer assembly by providing a marker and locking device which remain outside the patient but which can identify and fix the sheath such that the distal end of the introducer assembly remains at the correct position within the patient during the medical procedure. This can be particularly important in the deployment of implantable medical devices in position sensitive areas, for instance adjacent or at branch vessels or at bifurcations. The preferred embodiments disclosed below describe the positioning of a vena cava filter adjacent the renal veins.

Preferably, the coil has an inner diameter when unbiased which is the same as or less than an outer diameter of the sheath or catheter. This structure of locking device, it has been found, is particularly effective for sheaths and similar components having a relatively low radial strength. The locking device can apply a substantially even radial force around the entire circumference of the element, which reduces the chances of collapse of the element.

It is preferred that the coil spring includes a plurality of turns, such as least two to five turns. Advantageously, the turn or turns of the coil form the inner surface of the positioning device.

The coil is preferably formed from a wire made with or provided with a biocompatible material or coating.

According to another aspect of the present invention, there is provided a method of fixing the location of a sheath or catheter in a patient, by means of an assembly which includes a positioning device locatable around the sheath or catheter, the positioning device including a locking device configurable between a releasing condition and a locking condition; the sheath or catheter including a distal end locatable in a patient and a proximal end which is maintained outside a patient during treatment; method including the steps of:

introducing percutaneously the sheath or catheter into a patient;

determining the location of the distal end of the sheath or catheter in the patient;

moving the positioning device along the proximal end of the sheath or catheter until the positioning device is located against the patient's skin at the percutaneous entry point;

locking the positioning device onto the sheath or catheter, thereby to fix the position of the distal end of the sheath or catheter in the patient.

In other words, the locking device fixes the length of the sheath which can be inserted into the patient.

Advantageously, the positioning device is located in a locked condition on the sheath or catheter prior to its introduction into a patient, the method including the step of releasing the positioning device once the sheath or catheter has been positioned in the patient, moving the positioning device to the percutaneous entry point and re-locking the positioning device.

Also described is a positioning device for securing the position of a medical device relative to a patient; the device including a coil spring provided with a plurality of turns and having first and second free ends terminating in first and second release tabs respectively, and a spring housing for holding the coil spring, the housing having first and second manually operable gripper panels or handles coupled to the first and second release tabs, the turns of the coil providing a channel through which an element to be held by the positioning device is locatable.

Preferably, the device is releasable by application of pressure against the tabs which causes the turns of the spring to expand.

The device advantageously includes a spring housing for holding the coil spring, the housing having first and second gripper panels or handles coupled to the first and second release tabs.

It is preferred that the turns of the coil form the inner surface of the positioning device.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
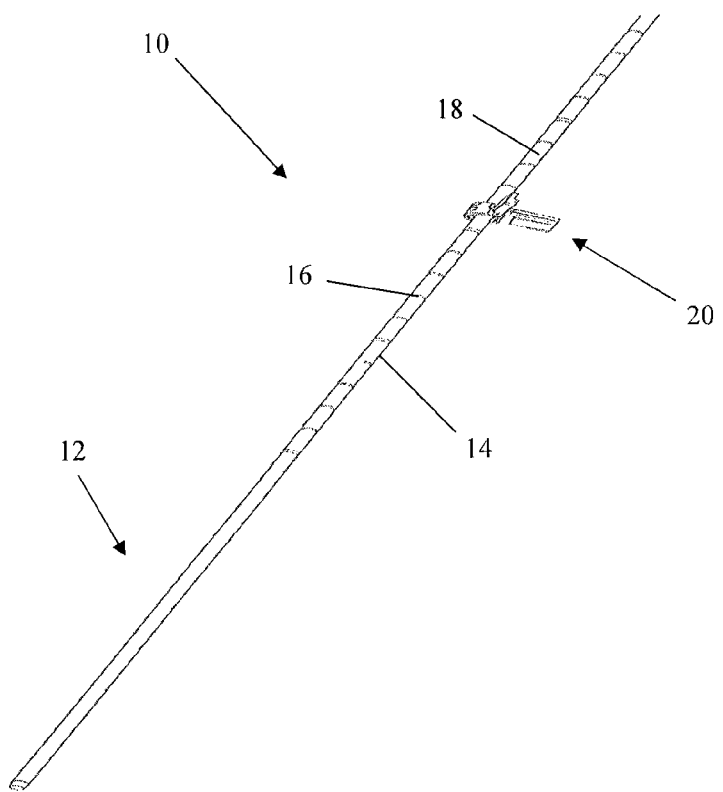
FIG. 1 shows a perspective view of the distal end of an introducer assembly according to an embodiment of the present invention.

Referring first to FIG. 1, there is shown the distal end 12 of an introducer assembly 10 used, in this example, for the implantation of a vena cava filter within a patient. A general view of the major components of the entirety of the introducer assembly 10 can be seen in FIGS. 3 to 5, described in further detail below.

The introducer assembly 10 includes a sheath 14 of substantially conventional form and which holds the other components of the introducer assembly. These components typically include the medical device to be deployed, an inner catheter or cannula which carries the medical device, release elements such as trigger wires or the like for releasing the medical device from the carrier catheter or cannula and, as appropriate, a guide wire used for guiding the endoluminal insertion of the introducer 10 into the patient.

In this embodiment, although not essential, the sheath 14 is provided with a plurality of markers 16 which extend preferably at regular intervals 18 over at least a part of the length of the sheath 14. The markers 16 may be in the form of bands extending circumferentially around the sheath 14 and in the preferred embodiment are aligned to the orthogonal to the longitudinal axis of the sheath 14, although could be in the form of a spiral or coil extending along the sheath. In their simplest form, the markers 16 may be painted on the outside of the sheath 14. In other embodiments, the bands could be grooves or cuts on the outer surface of the sheath 14 or otherwise incorporated into the structure of the sheath 14, for example as a part of a layer of the sheath 14.

The marker elements 16 preferably extend for a substantial portion of the length of the sheath 14 and in particular along a zone of the sheath 14 which would normally be located around the percutaneous entry point for the introducer assembly 10. In the embodiment shown in FIG. 1, the marker bands 16 do not extend over the distal end 12 of the introducer assembly 10, this being a portion of the sheath 14 which will always be located within the patient during the medical procedure.

In some embodiments, the marker elements 16 may also be radiopaque so as to be visible to ultrasonic imaging when the introducer assembly is located within the patient.

In all other respects, the sheath 14 can have a structure and characteristics equivalent to conventional introducer assembly sheaths known in the art.

There can be seen in FIG. 1, located around the sheath 14, a positioning device 20 for use in securing the position of the sheath 12 within a patient during the medical procedure, as disclosed in detail below. A preferred embodiment of the positioning device 20 can be seen in FIG. 2, to which reference is now made.

The positioning device 20 includes a coil spring 22 which has, in this embodiment, five turns 24 of coil arranged adjacent one another to form a channel or lumen 26 therewithin. The turns 24 form an inner surface 28 to the positioning device 20.

Figure 2:
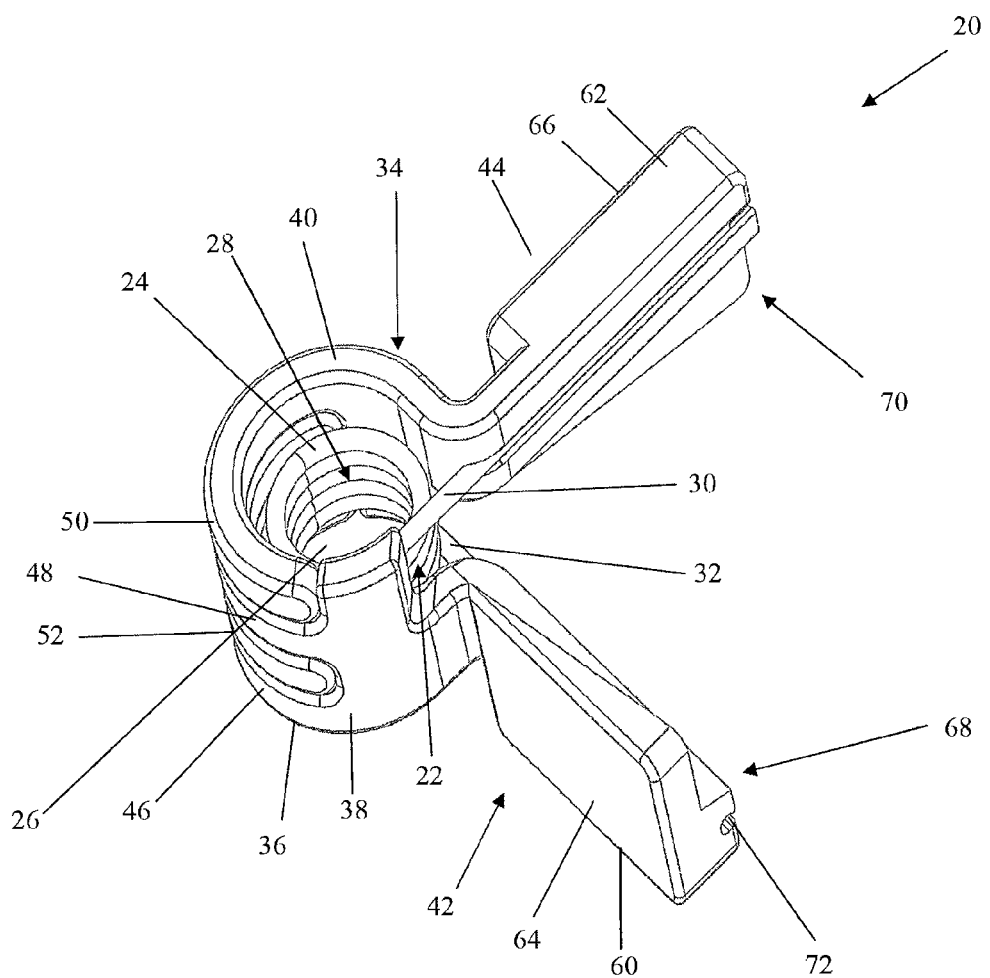
FIG. 2 is a perspective view of the preferred embodiment of positioning device for the introducer assembly of FIG. 1.

The ends of the coil 22 are in the form of first and second tabs or legs 30, 32 which extend at an angle to one another, from around 45 degrees to over 90 degrees as shown, for instance, in the example of FIG. 2.

The coil spring 22 is held within a case 34 which includes, in this embodiment, a generally cylindrical housing portion 36 which, in the configuration shown in FIG. 2, is substantially cylindrical and envelops the turns 24 of the coil spring 22 but which is open at either end so as to allow access to the channel 26 formed by the turns 24 of the coil spring 22. It is preferred that the housing portion 36 has a length, when viewed along the direction of the superposed turns 24, which is greater than the combined length of the turns 24.

In the embodiment shown in FIG. 2, the housing portion 36 is made of first and second partially rounded components 38, 40, each forming a part of a respective half 42, 44 of the casing 34. Each of the components 38, 40 includes, in this embodiment, interdigitating fingers 46-52 which, when interdigitated as shown in FIG. 2, form the cylindrical shape of the housing portion 36.

Each casing half 42, 44 also includes, extending from its respective component 38, 40, a handle or gripper pad 60, 62 (herein after called pad). Each pad 60, 62 includes an outer surface 64, 66 which in this embodiment is substantially flat and of size that it can easily be operated by the fingers of a user. Each pad 60, 62 also includes, on what could be termed the opposing internal surface 68, 70, a channel or recess 72, 74 running substantially lineally therealong and having in this example a generally cylindrical internal shape. Each channel 72, 74 is sized so as to receive substantially securely therewithin a respective one of the tabs or legs 30, 32 of the coil spring 22.

In the preferred embodiment, the tabs or legs 30, 32 of the coil spring 22 are a tight fit in their respective channels 72, 74, such that this fit secures the coil spring 22 to the casing 34.

The positioning device 20 of FIG. 2 is shown in what could be termed an unbiased configuration. In this configuration the coil spring 22 is held in tension, that is in a condition in which its legs 30, 32, as a result of residual tightening applied to the coils 24, still impart an opening force which biases the pads 60, 62 outwardly and as a result the interdigitating fingers 46, 52 towards one another into a closing configuration. This residual compression of the coil spring 22 ensures that the two halves 42, 44 of the casing 34 are substantially solid with one another. Hence, in this configuration the coil spring 22 ensures that the two handles 60, 62 are kept in what could be termed their outermost positions as shown in FIG. 2. In a practical embodiment, the spring legs 30, 32 have a completely unbiased rest angle of 95 to 100 degrees, whereas the casing handles a maximum angle of opening of 90 degrees. Thus, the legs 30, 32 will be left slightly pressed together in the casing.

Closing pressure applied to the outer surfaces 64, 66 of the two pads 60, 62 will urge the tabs or legs 30, 32 towards one another (in particular by rotating these around the turns 24 of the coil spring 22). So doing, it will be appreciated, will open the turns 24 of the coil spring 22, against the spring force generated by the spring, and thus increase the diameter of the channel 26. Of course, so doing will tension the coil spring 22 further, thereby providing a biasing force against pressure applied to the handles 60, 62, which will act to close the coil 22 again when the force applied to the pads 60, 62 is released.

When the pads 60, 62 are pressed together in the described manner, the fingers 46-52 of the housing portions 36 will rotate away from one another, thus also resulting in an increase in the diameter of the housing portion 36. It is preferred that the fingers 46-52 remain interdigitated within one another, thereby to assist and guide in the closure of the housing portion 66 when pressure on the pads 60, 62 is eventually released.

Thus, when the pads 60, 62 are pressed, in other words when the positioning device 20 is actuated, the channel 26 within the turns 24 of the coil 22 widens (as does the housing portion 36). When the pads 60, 62 are released, the coil spring 22 urges the positioning device 20 back into the configuration shown in FIG. 2 and in which the channel 26 regains its minimum diameter, determined by the fingers 46, 50 coming into abutment with the surfaces of the housing portion 56 between the respective fingers.

Referring again to FIG. 1, the sheath 14 has, in the preferred embodiments, a substantially uniform outer diameter particularly over the portion of the sheath 14 in the region of the percutaneous entry point of the patient, that is over that portion along which the positioning device 20 is held and located in use. Other parts of the sheath, for instance the distal end 12, could have a different outer diameter, for instance to give the sheath differing flexure characteristics.

The sheath 14, in the region of use of the positioning device 20, that is in region of the markings 16, has an outer diameter which is greater than the diameter of the channel 26 formed by the internal surface 28 of the coils 24 of the coil spring when the coil spring is in the unbiased condition shown in FIG. 2, that is when the pads 60, 62 are in their released positions. On the other hand, when the pads 60, 62 are brought towards one another in order to increase the diameter of the turns 24, the channel 26 has a larger diameter than the outer diameter of the sheath 14. Thus, when the pads 60, 62 are pressed towards one another, the positioning device 20 is able to slide along the sheath 14, whereas when the pads are released, the coils 24 wrap tightly around the sheath 16 and thus lock the device 20 to the sheath 14. When so locked, the device 20 cannot be inadvertently moved relative to the sheath 14 unless and until the handles 60, 62 are pressed again so as to open the coil 24. In some embodiments adequate positioning can be achieved by coils 24 which have an internal diameter in the unbiased condition which is substantially the same as the outer diameter of the sheath 14, by still providing friction against movement of the device 20 along the sheath 14. It is, however, preferred that the internal diameter of the coil 24 is smaller than the external diameter of the sheath 14.

The turns 24 of the coil spring 22 thus act as a locking device to lock the positioning device 20 to the sheath 14. The device can therefore be set to have a locking condition, shown in the configuration of FIG. 2, which locks the device to the sheath 14 and a releasing condition, where the tabs 60, 62 are pressed towards one another, allowing the positioning device 20 to be moved along the sheath.

The design of the coil spring 22, or locking device, in particular the turns of the coil 24, provides a particularly advantageous locking mechanism in connection with sheaths and other catheters used for implantable medical devices. More particularly, the general desire in the art is to make outer sheaths 14 and other catheters as thin as possible in order to give the introducer assembly a small diameter, while maintaining kink resistance, pushability, trackability and so on. However, these desirable characteristics of sheaths make them less able to withstand radial compressive forces. The coil spring 22, in particular when this has a plurality of turns 24, applies a substantially even radial compressive force to the sheath 14 in all radial directions. This has a significant effect in that it is possible to apply a large enough force on the sheath 14 to provide the required locking action without causing collapse or squashing of the sheath 14. Specifically, the compressive pressure applied by the turns of the coil 24 does not allow any part of the sheath 16 to spread out and also does not apply any uneven compressive force to the outside of the sheath which would cause this to fold and collapse on itself. Thus, the positioning device 20 does not reduce the diameter of the sheath lumen, allowing unrestricted passage of elements through the sheath. Furthermore, the coil spring 22 does not scratch the surface of the sheath.

In this regard, the coil spring 22 can have any number of turns 24. It has been found that an optimal number of turns of the coil spring 22 is between 3 to 6, the embodiment of FIG. 2 having four turns 24 (specifically 3.75). A smaller number of turns will open more than a spring with a greater number of turns, although more turns makes the device more positionally stable.

The coil spring 22 can be formed of any suitable resilient wire, one example being spring steel. In some embodiments, the wire of the coil spring 22 may be provided with a biocompatible coating.

It is to be appreciated also that although the embodiment of FIG. 2 has a coil spring 22 made of round cross-section wire, the shape of the wire is not an essential characteristic. The wire may, for instance, have other transverse cross-sectional shapes, one example being substantially flat.

Figure 3:
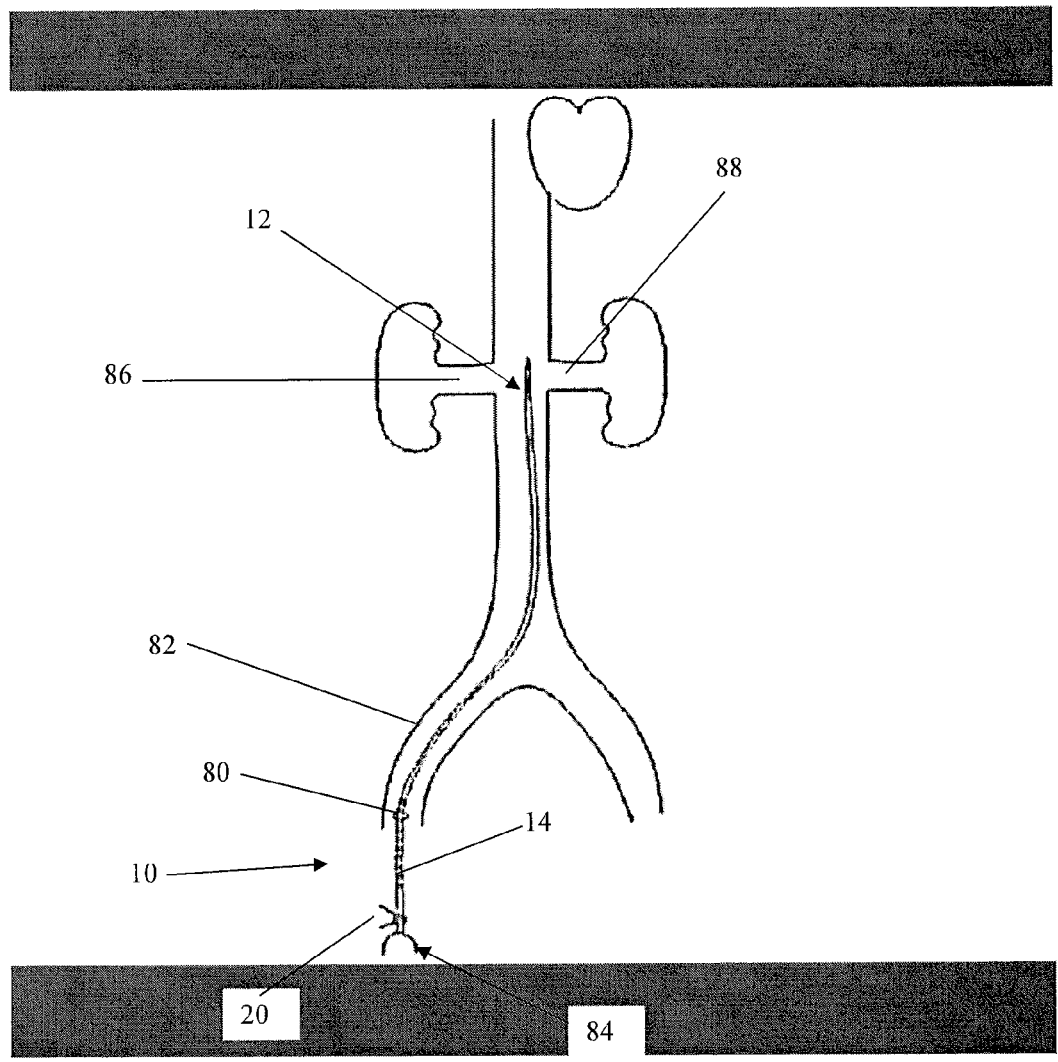
FIGS. 3 to 5 depict the preferred embodiment of introducer assembly during an operation for implanting a vena cava filter within the vena cava of a patient, just proximate the renal veins.
Figure 4:
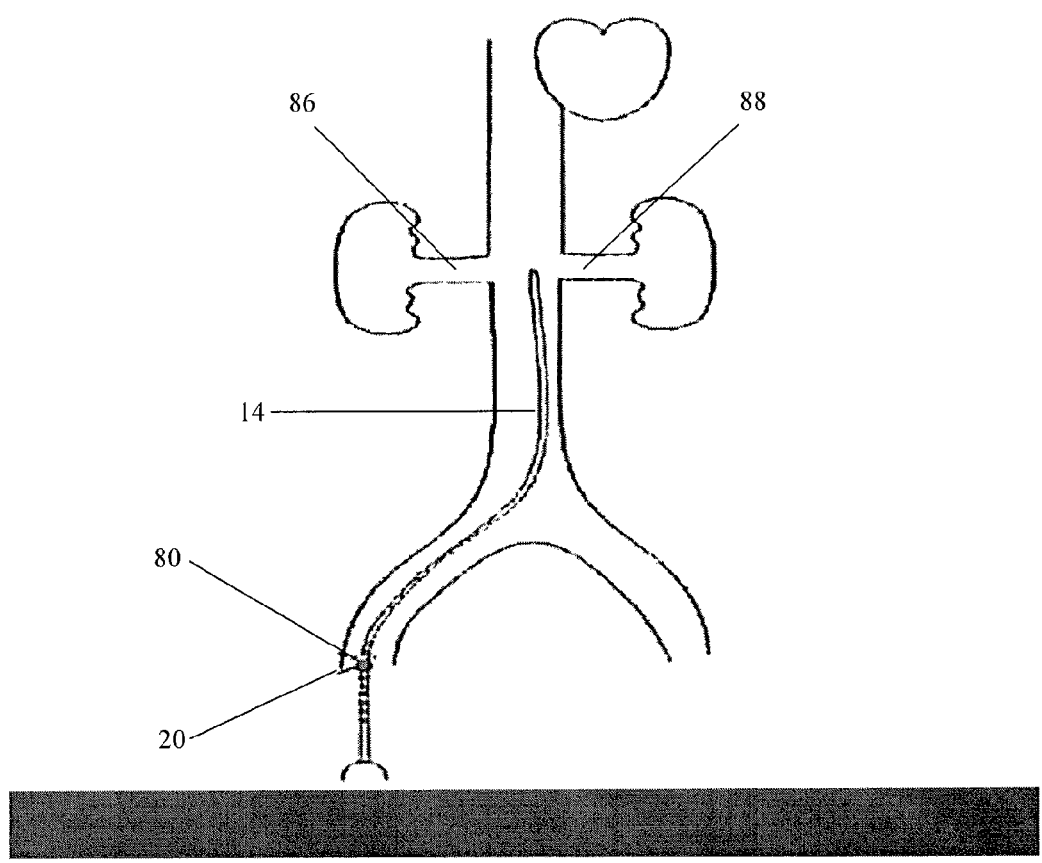
Figure 5:
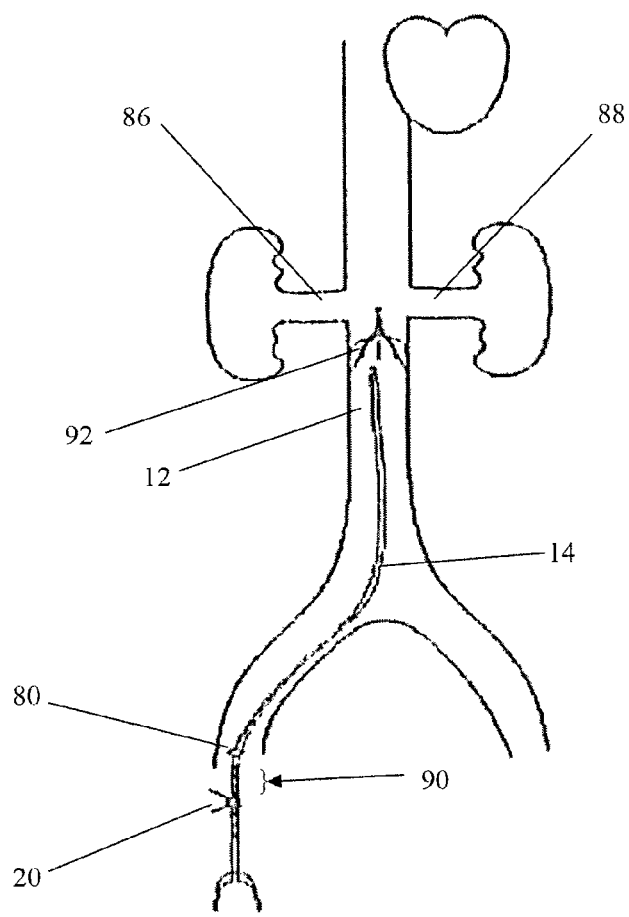

Referring now to FIGS. 3 to 5, the introducer assembly 10 is shown during the process of deployment of a vena cava filter just below the renal veins of a patient. The positioning device 20 of FIGS. 1 and 2 is used to mark the correct position of the sheath 14 and in particular the distal end 12 of the introducer assembly 10 within the patient. This is achieved in particular without the need to rely upon extensive imaging methods such as fluoroscopy, X-ray or CRT imaging and in the preferred embodiment using only ultrasonic imaging.

Referring to FIG. 3 first, the introducer assembly 10 is arranged such that the positioning device 20 is located on the sheath 14 at a proximal-most position. This ensures that the device 20 is kept out of the way during the percutaneous insertion of the sheath 14 into the patient through percutaneous entry point 80, in this example by the patient's femoral vein 82. In FIG. 3, the positioning device 20 is shown adjacent the external manipulation unit 84 of the introducer assembly 10.

The deployment procedure shown in FIGS. 3 to 5 first introduces the sheath 14 into the patient, by means of a guide wire and dilator (neither of which is shown). Once approximately positioned within the patient, the dilator is replaced with an intravascular ultrasound (IVUS) catheter, used to locate the renal veins 86, 88. In a particular embodiment, this is achieved by pushing the sheath and IVUS catheter though the patient's vasculature, close to the heart (thereby to confirm location in the correct vessels of the patient). Subsequent to this, making use of the visibility of the IVUS catheter under ultrasonic imaging, the sheath is pulled back until it is determined that the distal end of the IVUS catheter, and as a result thereof the distal end 12 of the sheath 14, is just below the level of the lowest renal vein 86 or 88. When this has been achieved, the positioning device or clip 20 is unlocked (that is, the handles or pads 60, 62 are pressed together) and this is then slid into abutment against the patient's skin at the percutaneous entry point 80, as shown schematically in FIG. 4. The positioning clip 20 is then relocked by releasing the tabs 60, 62, which causes the coils 24 to press and lock onto the sheath 14. The clip 20 can thus no longer be moved along the sheath 14 and therefore prevents the sheath 14 being inserted any further into the patient, in other words the length of sheath which can then be located in the patient. In the example shown, the distal end 12 of the sheath 14 cannot be moved beyond the renal veins 86, 88 while the positioning clip 20 is locked in place.

The markings 16 on the outside of the sheath 20 remain visible outside of the patient, as shown in FIGS. 3 to 5, and can give the clinician a coarse indication of the length of sheath 14 which is within the patient and thus whether the introducer is generally correctly positioned.

The markings 16 also provide a scale or measure useful in the deployment operation, as described below.

Once the sheath 14 has been correctly positioned within the patient and is fixed by means of the positioning clip 20, the medical device can be implanted into the patient. In this example a vena cava filter is fed into the sheath 14, carried on a carrier catheter of a type known in the art. Once the carrier catheter with the implantable medical device has been fully inserted into the sheath 14, that is once the implantable medical device is at the distal end 12 of the sheath 14 and ready for deployment, the sheath 14 can be retracted, in known manner, to release and deploy the medical device. In this instance, the positioning device or clip 20 provides a useful indication of the distance by which the sheath 14 is retracted to effect deployment of the medical device. Specifically, the clinician will know the length of the medical device on the carrier catheter and thus the amount by which the sheath must be retracted to expose the device. The marker bands on the sheath, being preferably set in a length scale, will give the clinician an indication of how far the sheath has been retracted (the distance between the locked positioning clip 20 and the percutaneous entry point 80) and thus whether the sheath 14 has been retracted sufficiently.

An example is shown in FIG. 5, where it can be seen that the retraction of the sheath 14 by distance 90 is sufficient to effect deployment of the vena cava filter 92 just below the renal veins 86, 88. Hence, the state of deployment can be determined by the measure of the gap 90, whereas the positioning of the medical device 92 just below the renal veins 86, 88 can be assured by the use of the positioning clip 20 and the fact that with the clip 20 properly positioned and locked it is not possible for the clinician to push the sheath 14 further into the patient.

Thus, the system provides a reliable way to use components of an introducer assembly which are not necessarily visible under ultrasonic imaging. This is particularly advantageous in connection with the deployment of medical devices which are position sensitive, for instance which are optimally positioned close branch veins or arteries, as is in the example shown in FIGS. 3 to 5. In connection with the vena cava filter 92 of the example of FIG. 5, the apparatus and method of use of the apparatus can ensure that no part of the vena cava filter 92 overlies either of the renal veins 86, 88, which could cause mis-orientation and/or misplacement of the vena cava filter 92 and as a result malfunction of the device.

Although FIGS. 3 to 5 are related to the placement of a medical device within the vena cava of a patient, it will be appreciated that the apparatus and deployment method disclosed herein are equally suitable for the deployment of other medical devices in other locations within a patient and may also be used in connection with other medical procedures which do not just involve the placement of an implantable medical device. The apparatus and system, could for instance, be used for vascular dilatation procedures, vascular occlusion, angioplasty procedures, for effecting medical treatments and so on.

It is to be understood that only some embodiments are described above which would be apparent to the skilled person having regard to the teachings herein and that the described embodiments are not intended to be limiting of these teachings.

Although the claims are set out in single claim dependent form, it is to be understood that the claimed and disclosed features herein can be combined with one another and that the claims are intended to interpreted as covering these combinations as if they were in multiple dependent form.

The invention claimed is:

1. An introducer assembly including a sheath or catheter having a lumen and designed for endoluminal placement in a patient, and a positioning device locatable around the sheath or catheter, the positioning device including a locking device configurable between a locking condition and a releasing condition and including a coil spring provided with at least one turn, wherein the sheath or catheter is locatable within the at least one turn of the coil, the positioning device being movable along the sheath or catheter when the locking device is in the releasing condition and being fixed in position on the sheath or catheter when the locking device is in the locking condition, the at least one turn applying a substantially even radial compressive force to the sheath or catheter in all radial directions such that when in the locking condition the positioning device does not reduce the diameter of the sheath or catheter lumen, the positioning device being operable to mark and fix a percutaneous entry point of the sheath or catheter so as to fix the position of the latter in the patient, wherein the coil spring comprises first and second free ends terminating in first and second release tabs respectively, and including a spring housing for holding the coil spring, the housing having first and second gripper panels coupled to the first and second release tabs.

2. An assembly according to claim 1, wherein the coil has an inner diameter when unbiased which is the same as or less than an outer diameter of the sheath or catheter.

3. An assembly according to claim 1, the coil spring includes a plurality of turns.

4. An assembly according to claim 3, wherein the coil spring includes at least two turns.

5. An assembly according to claim 3, wherein the coil spring includes one: of four, five or six turns.

6. An assembly according to claim 1, wherein the turn or turns of the coil form the inner surface of the positioning device.

7. An assembly according to claim 6, wherein the coil is formed from a wire provided with a biocompatible coating.

8. An assembly according to claim 1, wherein the locking device has, when in a unbiased configuration, an inner diameter the same as or smaller than an outer diameter of the sheath or catheter.

9. An assembly according to claim 1, wherein the sheath or catheter is provided with positioning markings on an outer surface thereof.

10. An assembly according to claim 1, including a deployment unit for deploying an implantable medical device in a patient through the sheath or catheter.

11. An assembly according to claim 10, wherein the deployment unit carries a vena cava filter for location in a patient.

12. An assembly according to claim 1, wherein the spring housing includes first and second partially rounded components, each component including interdigitating fingers which form a cylindrical shape corresponding to the at least one turn of the coil.

13. An assembly according to claim 12, wherein the interdigitating fingers come into abutment with respective surfaces of the spring housing when pressure against the tabs is released, thereby to restore the cylindrical shape.

14. An assembly according to claim 13, wherein the abutment of the interdigitating fingers holding the coil spring in residual tension in an unbiased configuration.

15. An assembly according to claim 14, wherein the residual tension biases the first and second gripper panels outward.

16. An assembly according to claim 15, wherein the sheath or catheter is provided with positioning markings on an outer surface thereof.

17. An assembly according to claim 1, wherein the positioning device is releasable by application of pressure against the tabs which causes the at least one turn of the spring to expand.

18. A assembly according to claim 1, wherein the coil spring is provided with at least three turns.

19. An assembly according to claim 1, wherein the spring housing holds the coil spring in residual tension in an unbiased configuration.

20. An assembly according to claim 19, wherein the residual tension biases the first and second gripper panels outward.

* * * * *